United States Patent [19]
Diamond et al.

[11] Patent Number: 6,063,038
[45] Date of Patent: May 16, 2000

[54] DEVICES AND METHODS FOR COLLECTING FECAL ANTIGEN SPECIMENS

[75] Inventors: Ronald N. Diamond, Anaheim Hills; Phillip C. Miller, Dana Point; William A. Stark, Costa Mesa, all of Calif.

[73] Assignee: CLMP, Inc., Wilmington, Del.

[21] Appl. No.: 09/289,158

[22] Filed: Apr. 9, 1999

[51] Int. Cl.[7] .................................................. A61B 10/00
[52] U.S. Cl. .......................................... 600/569; 600/576
[58] Field of Search .................................. 600/562, 569, 600/572, 576

[56] References Cited

U.S. PATENT DOCUMENTS

| | | | |
|---|---|---|---|
| 3,792,699 | 2/1974 | Tobin et al. | 600/572 |
| 3,862,013 | 1/1975 | Pagano | 600/572 |
| 4,017,601 | 4/1977 | Hilleman et al. . | |
| 4,200,690 | 4/1980 | Root et al. . | |
| 4,424,279 | 1/1984 | Bohn et al. | 436/534 |
| 5,212,062 | 5/1993 | Daniels et al. . | |
| 5,338,660 | 8/1994 | El Baby et al. . | |
| 5,543,115 | 8/1996 | Karakawa | 600/572 |

OTHER PUBLICATIONS

Orion Diagnostica: *Detection of fecal occult blood*; pp. 1–2; downloaded Mar. 14, 1999 www.diagnostica.orion.fi/products/infection/fecal.html.
Orion Diagnostica: *Rotavirus and adenovirus enteritis*; pp. 1–3; downloaded Mar. 14, 1999 www.diagnostica.orion.fi/products/infection/enteritis.html.

Primary Examiner—Cary O'Connor
Assistant Examiner—Pamela L. Wingood
Attorney, Agent, or Firm—Stout, Uxa, Buyan & Mullins, LLP; Donald E. Stout

[57] ABSTRACT

A fecal antigen specimen tube apparatus preferably consists of a 16×75 mm screw-top specimen tube and a special screw cap assembly. The screw cap has a hollow "straw" with a specimen collection brush on the end. The screw-cap assembly can be removed from the specimen tube so that the brush end may be dipped into a fecal sample and rotated to collect a specimen. The cap assembly with specimen is then screwed back into the specimen tube to seal the container. The straw preferably has a number of openings along its length, which permits fluid to move back and forth through the straw as the specimen tube is agitated. Filters with pore sizes of approximately 100 microns are disposed over the openings to prevent larger pieces of fecal matter from penetrating into the straw. The filter, however, will permit most parasites to pass into the straw. The top of the straw (and cap assembly) is preferably sealed with a heat-seal film. This film seals the specimen tube, preventing spillage and evaporation. The film can be penetrated by a sample probe of an automated instrument for removal of a portion of the liquid during the analytical process. After specimen processing, the tube may be resealed with tape or disposed of. Advantageously, then, the inventive device permits semi-automated specimen processing, which provides for a complete system from specimen collection to introduction on automated immunodiagnostic instruments.

30 Claims, 1 Drawing Sheet

DEVICES AND METHODS FOR COLLECTING FECAL ANTIGEN SPECIMENS

FIELD OF THE INVENTION

The present invention relates to the field of identification and analysis of parasites in mammals, and more particularly to systems and methods for detecting antigen antibodies which indicate the presence of certain parasites using semi-automated techniques.

BACKGROUND OF THE INVENTION

Identification and analysis of parasites in mammals often involves a large degree of manual preparation and analysis of specimens. The most common identification techniques involve optical microscopy, which is a very labor-intensive practice. Recently, alternate analytical methods involving antigen-antibody detection techniques have been shown to provide identification of certain parasites. These alternate techniques are amenable to automated methods, but so far have been carried out manually.

One prior art product which is presently available is a HEMOLEX Sampling Set (Cat. No. 67281) available from Orion Diagnostica of Finland. This set comprises a vial having a reagent contained therein, a stick for collecting a fecal sample, with a large cap at the top thereof which threadedly engages the vial, and a filter disposed at an upper end of the stick. To collect a specimen, the vial is opened, and the stick is inserted into the feces to be sampled. Once the fecal specimen has been collected on the end of the stick, the stick is inserted into the vial, after which the large cap is threadedly engaged with the vial to seal the vial, and the vial is shaken vigorously to mix the sample in the liquid reagent. The closed vial is then sent by the practitioner to a laboratory for analysis. To analyze the sample, a small cap disposed on the large cap directly over the upper end of the stick is opened, and the vial is inverted so that a small portion of the liquid sample mixture in the vial flows around the stick and exits through the small cap opening after passing through the filter at the top of the stick directly below the small cap opening. The filter ensures that the sample which exits the vial onto a test slide or the like does not include excessively large pieces of fecal material.

Typically, the laboratory will analyze the submitted fecal sample using an immunochemical test for the detection of native human hemoglobin therein, which is an indicator of fecal occult blood, detection of which is important in the diagnostic evaluation of patients with suspected gastrointestinal bleeding. However, similar fecal specimen testing filtration vials may be used to collect specimens for other diagnostic tests as well, such as detecting rotaviral or adenoviral antigens, for example. A problem with the Orion Diagnostic system is that it is only suitable for manual preparation and analysis of the fecal specimen.

What is needed, therefore, is a fecal antigen specimen collection apparatus which is easy and convenient to use and which is adapted for convenient use with automated immunodiagnostic instruments.

SUMMARY OF THE INVENTION

The present invention comprises a fecal antigen specimen tube apparatus which preferably consists of a 16 x 75 mm screw-top specimen tube and a special screw cap assembly. The screw cap has a hollow "straw" with a specimen collection brush on the end. The screw-cap assembly can be removed from the specimen tube so that the brush end may be dipped into a fecal sample and rotated to collect a specimen. The cap assembly with specimen is then screwed back into the specimen tube to seal the container. The straw preferably has a number of openings along its length, which permits fluid to move back and forth through the straw as the specimen tube is agitated. Filters with pore sizes of approximately 100 microns are disposed over the openings to prevent larger pieces of fecal matter from penetrating into the straw. The filter, however, will permit most parasites to pass into the straw. The top of the straw (and cap assembly) is preferably sealed with a heat-seal film. This film seals the specimen tube, preventing spillage and evaporation. The film can be penetrated by a sample probe of an automated instrument for removal of a portion of the liquid during the analytical process. After specimen processing, the tube may be resealed with tape or disposed of. Advantageously, then, the inventive device permits semi-automated specimen processing, which provides for a complete system from specimen collection to introduction on automated immunodiagnostic instruments.

More particularly, a fecal specimen collection apparatus is provided which comprises a tube having a sidewall and a cap assembly adapted for insertion into the tube, wherein the cap assembly comprises a cap and a straw portion extending downwardly from the cap. Also provided is a fecal specimen collection element, preferably a brush, disposed on a lower end of the straw portion. Advantageously, a filter is disposed on a lower end of the straw portion. The straw portion is hollow, and comprises a sidewall defining an interior volume. Because the filter is disposed on a lower end of the straw portion, all of the liquid mixture entering the interior volume thereof is filtered and available for use in an automated analysis system without the need for further filtration.

In another aspect of the invention, a fecal specimen collection apparatus is provided which comprises a tube having a sidewall and a cap assembly adapted for insertion into the tube. The cap assembly comprises a cap and a straw portion extending downwardly from the cap, in such a manner that an upper end of the straw portion extends through the cap. A fecal specimen collection element is disposed on a lower end of the straw portion and a top opening is disposed on an upper end of the straw portion, at a top end of the cap. A puncturable film is disposed over the top opening, so that the probe of an automated immunodiagnostic instrument may be inserted directed into the straw portion by puncturing the film.

In yet another aspect of the invention, there is provided a fecal specimen collection apparatus which comprises a tube having a sidewall and a cap assembly adapted for insertion into the tube, wherein the cap assembly comprises a cap and a straw portion extending downwardly from said cap. The straw portion comprises a sidewall defining a hollow interior and a filter disposed on said straw portion sidewall. The filter may comprise a plurality of small holes or pores molded directly into the sidewall of the straw portion, or alternatively, a separate element disposed over one or more larger holes in the straw portion sidewall.

In still another aspect of the invention, there is disclosed a method for collecting and analyzing a fecal specimen using an apparatus which comprises a tube having a sidewall and a cap assembly removably attachable to the tube, wherein the cap assembly comprises a cap and a straw portion extending through and downwardly from the cap. The straw portion has a sidewall which defines an interior volume, and a specimen collection element, preferably a brush, is disposed on a lower end of the straw portion. The method comprises the steps of inserting the cap assembly into a fecal sample so that a fecal specimen is collected by the specimen collection element, and inserting the cap assembly into the tube, sealingly securing the cap assembly to the tube, so that liquid contained in the tube and in the straw portion cannot escape from the apparatus. Then, the apparatus is agitated so that liquid reagent contained in the tube is mixed with the fecal specimen. When it is desired to complete an analysis of the specimen, immediately, or sometime later during the shelf life of the mixed liquid, a probe may be inserted into the straw portion without removing the cap assembly from the tube, for removing a portion of the mixed liquid contained in the straw portion for that analysis.

The invention, together with additional features and advantages thereof, may best be understood by reference to the following description taken in conjunction with the accompanying illustrative drawing.

BRIEF DESCRIPTION OF THE DRAWING

The FIGURE is a cross-sectional view of a fecal antigen specimen tube constructed in accordance with the principles of the invention.

DESCRIPTION OF THE INVENTION

Figure 1:
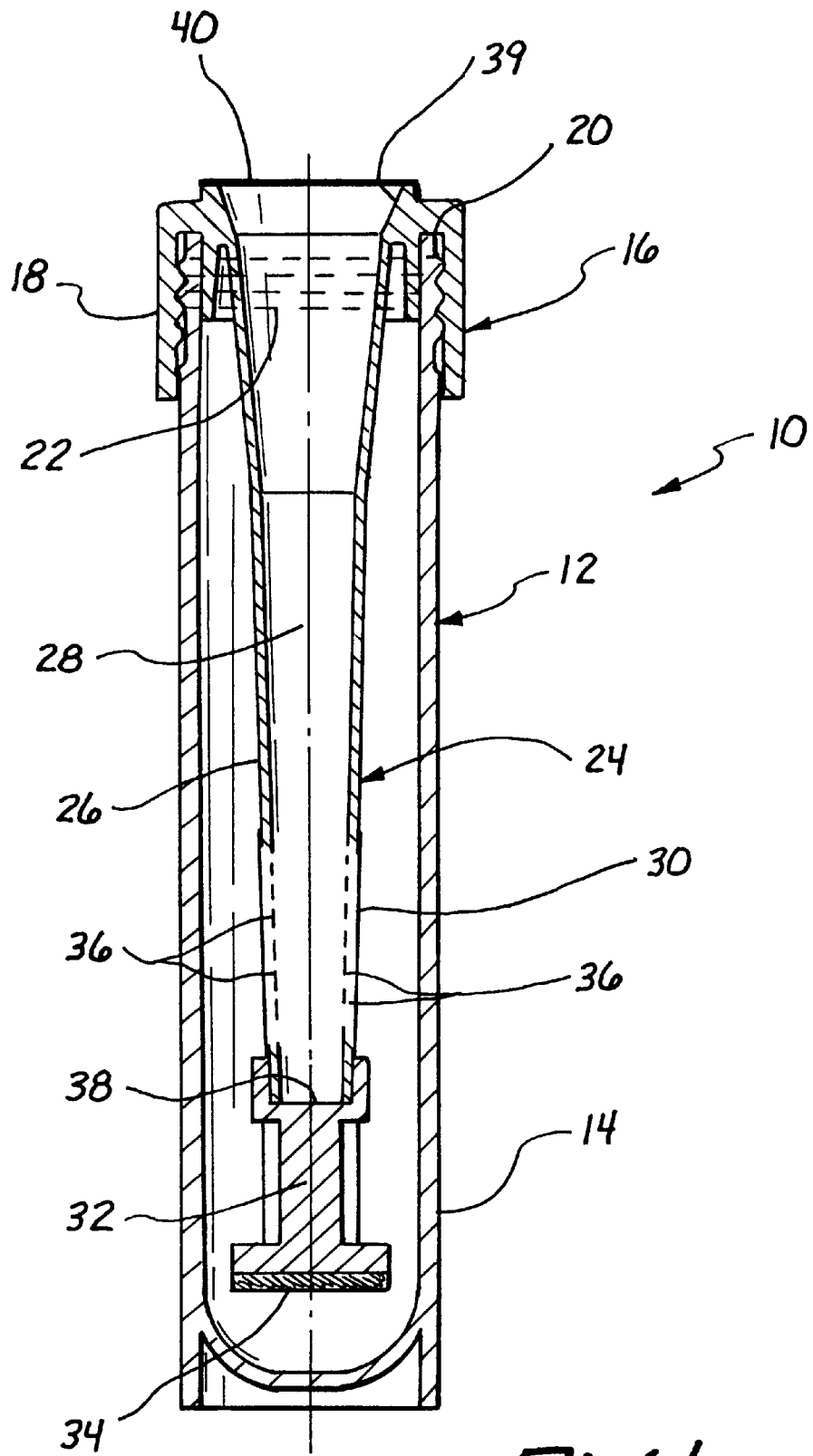

Referring now to the FIGURE, there is shown a fecal antigen specimen collection device 10, preferably comprising a cylindrical tube 12 having a cylindrical sidewall 14. A screw cap assembly 16 comprises a screw cap 18 having internal threads 20 which are adapted to engage external threads 22 on the upper end of the tube 12 to attach the screw cap to the tube. Of course, alternative engagement means may be employed, if desired, and the tube 12 may comprise other configurations as well. Attached to and descending downwardly from the screw cap 18 is a straw portion 24, which is hollow and has a cylindrical wall 26 defining an interior volume 28. Near the lower end of the straw portion 24 is a filter portion 30, which forms a part of the cylindrical wall 26. At the base of the straw portion 24 is a bracket 32, to which is attached a specimen collection brush 34.

In the preferred embodiment, the cylindrical tube 12 is 16 mm in diameter and about 75 mm in length, and is molded of a rigid inert plastic material, such as polypropylene. A number of openings 36 are disposed in the cylindrical wall 26, as shown in the FIGURE, along its length. The straw portion 24 is also preferably molded of polypropylene, or another suitable inert rigid material. The filter portion 30 is disposed over the openings 36 to prevent larger pieces of fecal matter from penetrating into the interior volume 28 of the straw 24. The interior volume 28 is enclosed at its bottom end by lower wall 38. The filter material preferably includes pore sizes of between about 50 and 150 microns, and more particularly approximately 100 microns, and preferred filter materials are precision woven plastic meshes and mesh assemblies available from Sefar America, for example.

Alternatively, instead of employing a separate filter portion 30 over the holes 36, the filter could be fabricated as part of the straw 24 by suitably constructed molding apparatus. Essentially, this would involve creating a sufficient number of holes 36 which are sufficiently small (i.e. between about 50 and 150 microns and preferably about 100 microns in diameter) so that they would directly perform the desired filtration function.

At the top end of the interior volume 28 of the tube 12, on the straw portion 24, is an opening 39, which is preferably sealed by a heat-seal plastic film 40. The upper end of the straw portion 24 extends through the cap 18, so that the opening 39 is approximately flush with a top surface of the cap.

In practicing the preferred method of the invention, a practitioner will remove the screw cap assembly 16 from the specimen tube 12 by disengaging the threads 20, 22. Then, the specimen collection brush 34 is dipped into a fecal sample and rotated to collect a suitable specimen. Following the collection of a specimen, the cap assembly 16 is re-inserted into the tube 12, with the threads 20 and 22 being engaged to seal the container. The heat seal film 40 seals the specimen tube, preventing spillage and evaporation. The interior volume 28 is pre-filled with a suitable liquid reagent or transport media as is well known in the art. Such transport media typically comprise a buffer and a preservative, such as sodium azide, and may also include a fixative. One such reagent is available from Orion Diagnostica. The tube 12 is shaken several times, to ensure that the liquid reagent and the fecal sample are thoroughly mixed within the interior volume 28. It is noted that the filter portion 30 preferably has pore sizes of about 100 microns, in order to ensure that the larger pieces of fecal matter do not penetrate into the straw portion 24. The filter, however, will permit most parasites to pass into the straw portion 24.

Advantageously, at any time following collection of the fecal specimen, during its shelf life, the film 40 can be penetrated by a sample probe of an automated instrument, such as an automated immunodiagnostic instrument available from Quest Diagnostics, Inc. and marketed as the Nichols Advantage® Specialty System. The sample probe functions to remove a portion of the liquid during the analytical process. After the specimen is processed, the tube may be resealed with tape or disposed of.

While this invention has been described with respect to various specific examples and embodiments, it is to be understood that the invention is not limited thereto and that it can be variously practiced within the scope of the following claims.

What is claimed is:

1. A fecal specimen collection apparatus, comprising:
   a tube having a sidewall;
   a cap assembly adapted for insertion into the tube, the cap assembly comprising a cap and a straw portion extending downwardly from said cap;
   a fecal specimen collection element disposed on a lower end of said straw portion; and
   a filter disposed on a lower end of said straw portion.

2. The fecal specimen collection apparatus as recited in claim 1, wherein said straw portion is hollow and comprises a sidewall defining an interior volume.

3. The fecal specimen collection apparatus as recited in claim 2, and further comprising at least one opening disposed on said straw portion sidewall.

4. The fecal specimen collection apparatus as recited in claim 3, wherein said filter is disposed on said straw portion sidewall over said at least one opening.

5. The fecal specimen collection apparatus as recited in claim 3, wherein said filter comprises said at least one opening.

6. The fecal specimen collection apparatus as recited in claim 1, wherein said fecal specimen collection element comprises a brush.

7. The fecal specimen collection apparatus as recited in claim 6, wherein said fecal specimen collection element further comprises a bracket disposed on a lower end of said straw portion, said brush being connected to said bracket.

8. The fecal specimen collection apparatus as recited in claim 2, and further comprising a top opening on said straw portion, said top opening being sealed by a puncturable film.

9. The fecal specimen collection apparatus as recited in claim 1, wherein said tube and tube sidewall are cylindrical.

10. The fecal specimen collection apparatus as recited in claim 2, wherein said cap assembly is removable from said tube as a single unit for collecting a fecal specimen, and then reinsertable into said tube to mix the fecal specimen with reagent contained in the tube.

11. A fecal specimen collection apparatus, comprising:
a tube having a sidewall;
a cap assembly adapted for insertion into the tube, the cap assembly comprising a cap hollow and a straw portion comprising a sidewall defining an interior volume, and extending downwardly from said cap, an upper end of the said straw portion extending through said cap;
a fecal specimen collection element disposed on a lower end of said straw portion;
a top opening disposed on an upper end of the straw portion, at a top end of said cap; and
a puncturable film disposed over said top opening.

12. The fecal specimen collection apparatus as recited in claim 11, wherein said puncturable film comprises a plastic film.

13. The fecal specimen collection apparatus as recited in claim 12, wherein said plastic film is sealed over said opening.

14. The fecal specimen collection apparatus as recited in claim 11, wherein said apparatus comprises a filter portion disposed on said sidewall.

15. The fecal specimen collection apparatus as recited in claim 14, wherein the filter portion has holes which are sufficiently small to prevent larger fecal pieces from entering the interior volume of the straw portion, but are sufficiently large to permit most parasites to enter the interior volume of the straw portion.

16. The fecal specimen collection apparatus as recited in claim 15, wherein said holes are sized within a range of 50–150 microns in diameter.

17. The fecal specimen collection apparatus as recited in claim 15, wherein said holes are approximately 100 microns in diameter.

18. The fecal specimen collection apparatus as recited in claim 14, wherein the filter portion comprises a precision woven plastic mesh material.

19. The fecal specimen collection apparatus as recited in claim 14, wherein said filter portion comprises a plurality of holes disposed in the sidewall of said straw portion.

20. The fecal specimen collection apparatus as recited in claim 14, wherein said sidewall includes a plurality of holes disposed therein, and said filter portion is disposed over said plurality of holes.

21. The fecal specimen collection apparatus as recited in claim 11, wherein said fecal specimen collection element comprises a brush.

22. The fecal specimen collection apparatus as recited in claim 19, wherein said fecal specimen collection element further comprises a bracket disposed on a lower end of said straw portion, said brush being connected to said bracket.

23. A fecal specimen collection apparatus, comprising:
a tube having a sidewall;
a cap assembly adapted for insertion into the tube, the cap assembly comprising a cap and a straw portion extending downwardly from said cap, the straw portion comprising a sidewall defining a hollow interior; and
a filter disposed on said straw portion sidewall.

24. The fecal specimen collection apparatus as recited in claim 23, wherein said filter comprises a plurality of holes disposed in said straw portion sidewall.

25. The fecal specimen collection apparatus as recited in claim 23, wherein said straw portion sidewall comprises at least one hole therein, and said filter is disposed over said at least one hole.

26. A method for collecting and analyzing a fecal specimen using an apparatus which comprises a tube having a sidewall and a cap assembly removably attachable to said tube, the cap assembly comprising a cap and a straw portion extending through and downwardly from said cap, the straw portion having a sidewall which defines an interior volume, and a specimen collection element disposed on a lower end of the straw portion, said method comprising the steps of:
inserting the cap assembly into a fecal sample so that a fecal specimen is collected by said specimen collection element;
inserting the cap assembly into said tube;
sealingly securing the cap assembly to said tube, so that liquid contained in said tube and in said straw portion cannot escape from the apparatus;
agitating the apparatus so that liquid reagent contained in said tube is mixed with said fecal specimen; and
inserting a probe into said straw portion without removing the cap assembly from the tube, for removing a portion of the mixed liquid contained in said straw portion for analysis.

27. The method as recited in claim 26, and further comprising removing the cap assembly from the tube prior to inserting it into the fecal sample.

28. The method as recited in claim 26, wherein the agitating step further comprises filtering said liquid reagent and fecal specimen mixture so that fecal solids introduced into the straw portion are not of excessive size.

29. The method as recited in claim 26, wherein the straw portion further includes a top opening which is covered by a sealing film, and the probe insertion step comprises puncturing the film with a distal end of the probe so that the probe enters the straw portion through said film.

30. The method as recited in claim 29, and further comprising the step of withdrawing the probe after obtaining a suitable portion of the mixed liquid contained in the straw portion, and the further step of re-sealing said top opening after withdrawing the probe, thereby preserving the portion of mixed liquid remaining in the straw portion for future analysis.

* * * * *